United States Patent
Zoltan

(10) Patent No.: US 8,662,078 B2
(45) Date of Patent: Mar. 4, 2014

(54) BI-FUNCTIONAL INHALING DEVICE

(75) Inventor: Pohl Zoltan, Brasov (RO)

(73) Assignees: Salt Pharma SRL, Brasov (RO); Exact RX Inc., Melvile, NY (US)

( * ) Notice: Subject to any disclaimer, the term of this patent is extended or adjusted under 35 U.S.C. 154(b) by 0 days.

(21) Appl. No.: 13/324,577

(22) Filed: Dec. 13, 2011

(65) Prior Publication Data
US 2012/0247463 A1    Oct. 4, 2012

(30) Foreign Application Priority Data
Apr. 4, 2011    (RO) .............................. A 2011 00297

(51) Int. Cl.
*A61M 15/00*    (2006.01)
*A61M 15/02*    (2006.01)

(52) U.S. Cl.
USPC .................................................... 128/203.15

(58) Field of Classification Search
USPC ............. 128/203.15, 203.19, 203.21, 200.14; 222/325
See application file for complete search history.

(56) References Cited

U.S. PATENT DOCUMENTS

| | | | |
|---|---|---|---|
| 7,100,605 B2 * | 9/2006 | Opitz ........................ | 128/202.25 |
| 7,360,537 B2 * | 4/2008 | Snyder et al. ............. | 128/200.23 |
| 2006/0283448 A1 * | 12/2006 | Edwards et al. .......... | 128/203.15 |
| 2007/0175476 A1 * | 8/2007 | Lipowicz .................. | 128/205.29 |
| 2008/0295834 A1 * | 12/2008 | Thoemmes et al. ...... | 128/203.21 |
| 2009/0123548 A1 * | 5/2009 | Tom .............................. | 424/489 |
| 2009/0165791 A1 * | 7/2009 | Wendland ................. | 128/203.21 |
| 2009/0260635 A1 * | 10/2009 | Dean ............................. | 128/863 |
| 2010/0101573 A1 * | 4/2010 | Foley et al. .............. | 128/203.15 |

FOREIGN PATENT DOCUMENTS

| | | |
|---|---|---|
| GB | 645645 | 11/1950 |
| RO | 108648 B1 | 7/1994 |
| RO | 122480 B1 | 7/1994 |
| RO | 117070 B | 10/2001 |

OTHER PUBLICATIONS

RO108648 Abstract.
RO122480 Abstract.
RO117070 Abstract.

* cited by examiner

*Primary Examiner* — Loan Thanh
*Assistant Examiner* — Jennifer M Deichl
(74) *Attorney, Agent, or Firm* — Hershkovitz & Associates, PLLC; Abraham Hershkovitz

(57) ABSTRACT

The bi-functional inhaling device has an elliptic shape in the frontal, lateral and transversal plane and includes a lower part and an upper part, a lower cap being located at the lower part to accommodate inside a cartridge made up of a lower cap, a strip of absorbent material, a body and an upper cap of the cartridge. An adapter for oral inhaling is mounted over the upper cap of the cartridge, the adapter being covered with a protection cap. An adapter for nasal inhaling is mounted over the upper cap of the cartridge. A membrane is secured on the base surface of the upper cap of the cartridge, the membrane having the role of a one-way valve. Natural salt crystals are introduced inside the cartridge, in the space created between the lower cap, the upper cap and the body of the cartridge.

19 Claims, 7 Drawing Sheets

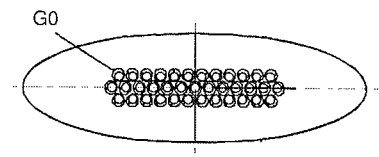
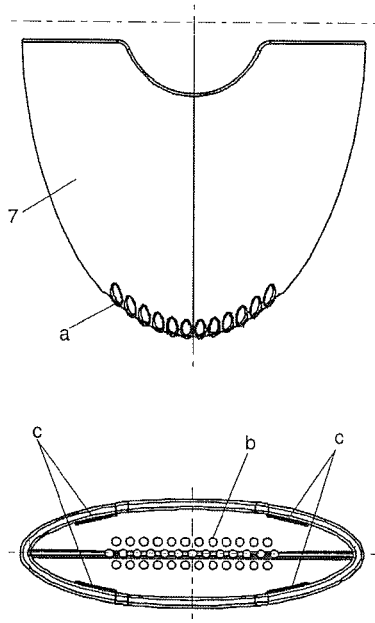
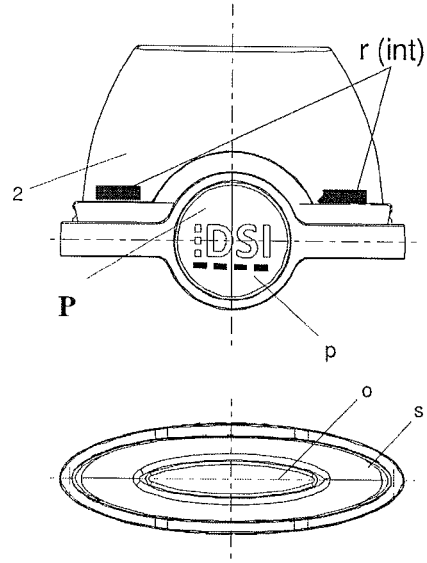
Fig. 3                                   Fig. 4
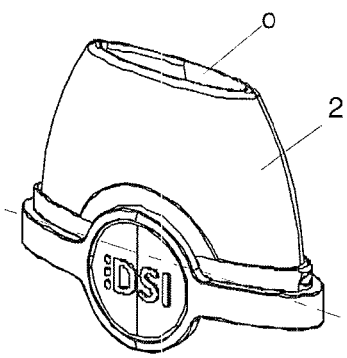
Fig. 5

BI-FUNCTIONAL INHALING DEVICE

CROSS-REFERENCE TO RELATED APPLICATIONS

This application claims priority under 35 U.S.C. §1.119 to Romanian Patent Application No. A/00297, filed Apr. 4, 2011, the disclosure of which is expressly incorporated by reference herein in its entirety.

BACKGROUND OF THE INVENTION

1. Field of Invention

The present invention refers to a bi-functional inhaling device for salt crystal therapy.

Natural therapies are presently more often used by patients as it has been worldwide ascertained that the side effects associated with these therapies are very low.

At the same time, natural therapies are recommended in addition to medicament-based treatments in order to reduce these treatments and the complications that may occur in different organs during said treatments.

The device disclosed within the present invention offers the possibility of an alternative therapy, recommended to patients suffering from bronchial asthma, pharyngitis, bronchitis or, allergic rhinitis, being considered a portable salt mine, the salt having effects on the respiratory tract by means of saline aerosols, therapy known ever since Hippocrates' time.

2. Description of the Related Art

Many types of inhalers are used in treating respiratory disorders, both for medicament-based and homeopathic treatment.

RO Patent No. 108648 discloses an inhaler for delivering a solid-based dosage, for instance powders with pharmaceutical activity, in an airflow absorbed by the user. The inhaler comprises a storage chamber wherein a dosing pin protrudes, said dosing pin being provided with dosing delivery means and said chamber and pin being movable with respect to each other such as, in a first position of the dosage pin and storage chamber, the dosing delivery means will be situated in the storage chamber where it will be filled with solids and, in its second corresponding position, the solids will be mixed with the airflow.

A powder inhaler for administering a single dose of medicinal products in granulate or powder form is known from RO Patent No. 117070, to relieve respiratory deficiency disorders. The inhaler comprises a casing whereon a mouthpiece is mounted, the mouthpiece being provided with an air inlet and a cartridge mounted within said casing which comprises an element made up of several compartments, each of them containing a dose of said medicament product. By moving the cartridge with respect to the air path, the medicament doses are discharged, the compartments being axially and angularly placed with respect to each other, such as to define a helical path.

Another document, namely RO Patent No. 122480, granted to the author of the present invention, refers to a dry powder inhaler comprising an upper part in the form of a truncated cone, provided with an aperture at the upper end and, a base at the lower end, said base being used as a filter, due to the presence of small-sized apertures, said base also having a central aperture wherein the leg of a mushroom-type valve is mounted, the rest of the valve being supported on the upper part base, the upper part being mounted on a lower part of a similar truncated cone form, provided, on its upper part, with an aperture similar in shape and, of the same size with the upper part base, at its lower end, said lower part being provided with a filter, wherein small-sized apertures are made, so as to allow the passage of an airflow inside. Within the cavity formed in the lower part, there are stored salt crystals in natural form that are crossed by the airflow inhaled by the user.

GB Patent No. 645645 discloses a nasal inhaler incorporated into a compact pocket structure, having a compartment containing said inhaler and, a passage adapted to communicate, on one hand, with the atmosphere and, on the other hand, with breathing apertures provided in a body suited for being applied on the nose, a blocking valve to prevent expired air from passing through the above-mentioned compartment, a passage for the expired air communicating with said apertures and, adapted to communicate with the exterior and, another blocking valve, to prevent inhaling air from said passage.

The prolonged use of medicament powder inhalers is known to lead to the occurrence of rashes within the oral cavity, as well as to other side effects. Therefore, homeopathic therapies using natural salt crystals obtained from worldwide acknowledged mines are more and more recommended by specialists.

At the same time, most of the known inhalers comprise components that require complex manufacturing technologies, the assembling thereof also involving qualified labor force.

The problem that the invention solves consists in treating the lower and upper respiratory airways by using aromatherapy in addition to saline therapy and aerosols, which results in an effective increase of the therapeutic effect, the aromatic and saline air reaching the upper respiratory tract.

SUMMARY OF THE INVENTION

This problem has been solved by the inventor by the conception of a bi-functional inhaling device, provided with a storage chamber for salt crystals, filters having apertures to allow the circulation of the inhaled airflow through the mass of salt crystals, a one-way valve and a mouthpiece adapted to the opening of the oral cavity, wherein said device has an elliptical shape in the frontal, lateral and transversal plane, being made of a lower part and an upper part with respect to the direction of circulation of the inhaled air, with a lower cap at the lower part of said device and further on progressing towards the upper limit of said device, with a cartridge located inside said cap, the cartridge comprising a cartridge lower cap, an absorbent material strip soaked with an essential oil (menthol, eucalypt, fir tree etc) used for aromatherapy, a cartridge body and a cartridge upper cap, and further on, if desired, with an adapter for nasal inhaling or an adapter for oral inhaling mounted to the upper part of the device, over the cartridge upper cap, the device being closed at its upper part with a protecting cap.

The advantages brought by the present invention consist in:
- It is a product manufactured from biocompatible materials of medical use or from PLA (Polylactic Acid) material, the later being biodegradable;
- It offers hygienic protection;
- The cartridge with natural salt crystals is interchangeable; the user does not need to buy another inhaler, but only the cartridge as such.
- The user has the possibility to select and use a plurality of cartridges, with or, without various essential oils, choosing the most effective and/or convenient variant;
- The interchangeable cartridges are easily adapted to the rest of the inhaling device;

The device components are mechanically secured, the adhesives present with known inhalers being eliminated, as such adhesives may contain chemical compounds that are harmful to health and cause a decrease in the therapeutic efficiency.

It can be easily assembled and disassembled in order to perform the hygienic cleaning of the components;

The adapters are of individual use and offer a considerable hygiene due to the protection cap, both for oral and nasal adapters;

The manufacturing costs are reduced.

BRIEF DESCRIPTION OF THE DRAWINGS

The bi-functional inhaling device is further disclosed with a reference to the FIGS. 1-15, which represent:

FIG. 3 a view of the device lower cap 7;

FIG. 4 views of the oral adapter 2;

FIG. 5 a perspective view of the oral adapter 2;

FIG. 12 view of membrane 6a;

DETAILED DESCRIPTION OF PREFERRED EMBODIMENTS

The bi-functional inhaling device according to the invention, intended for salt crystal therapy and aromatherapy, comprises a plurality of components assembled along the longitudinal direction I-I, thus forming the device. Whenever necessary, the device can be disassembled for hygienic cleaning followed by the reassembling of the said components.

The bi-functional inhaling device is manufactured of biocompatible PC (polycarbonate) materials of medical use or special biodegradable material (PLA PolyLactic Acid).

Each component is further disclosed individually with explanations of the role in the function of the device.

Figure 1:
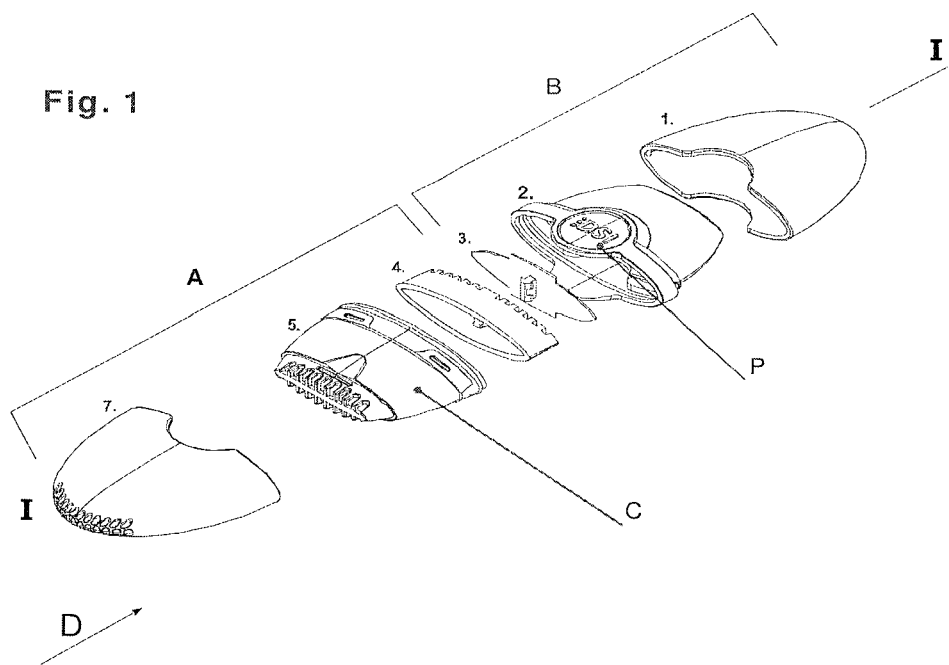
FIG. 1 a developed perspective view of the bi-functional inhaling device, with oral adapter.
Figure 2:
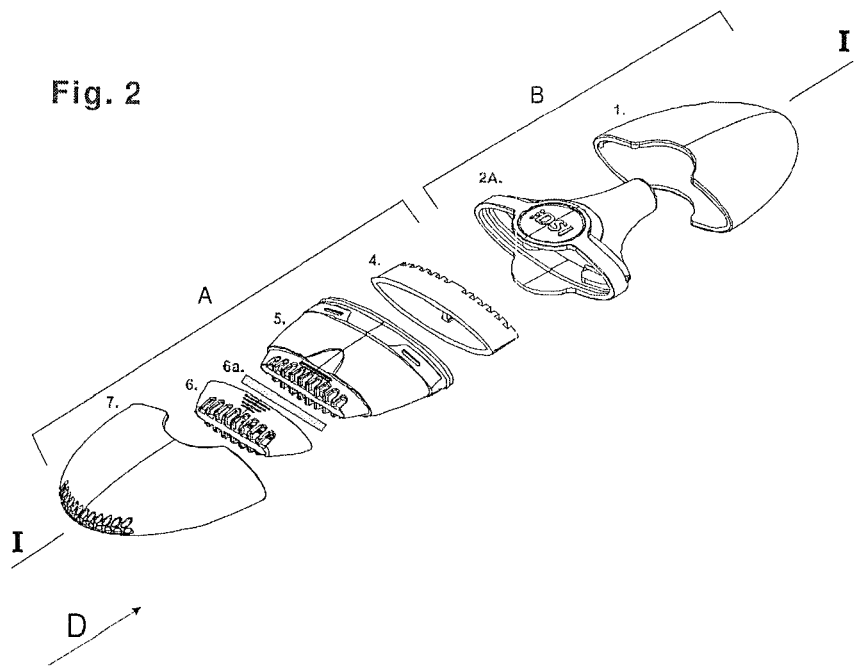
FIG. 2 a developed perspective view of the bi-functional inhaling device, with nasal adapter.
Figures 6, 7:
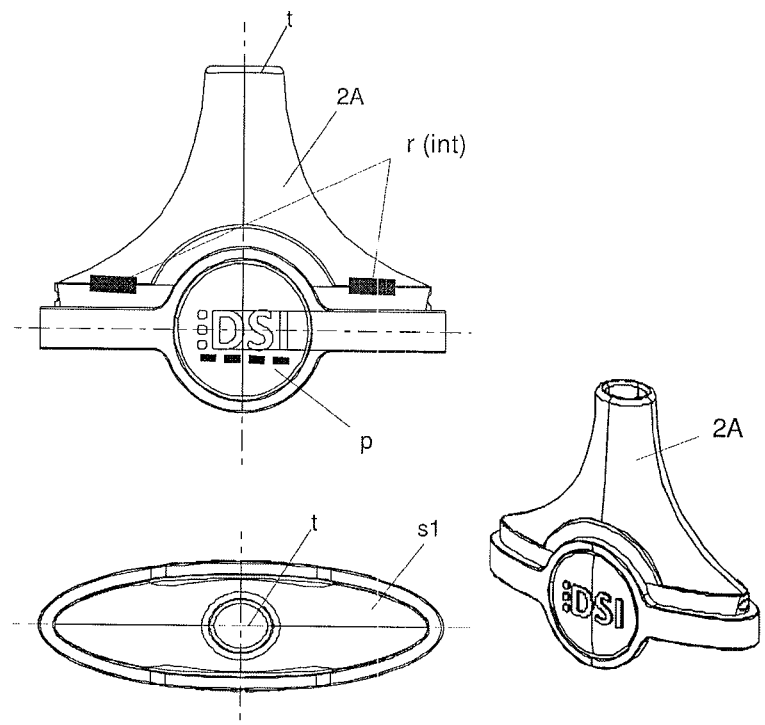
FIG. 6 views of the nasal adapter 2A.
FIG. 7 a perspective view of the nasal adapter 2A.
Figure 8:
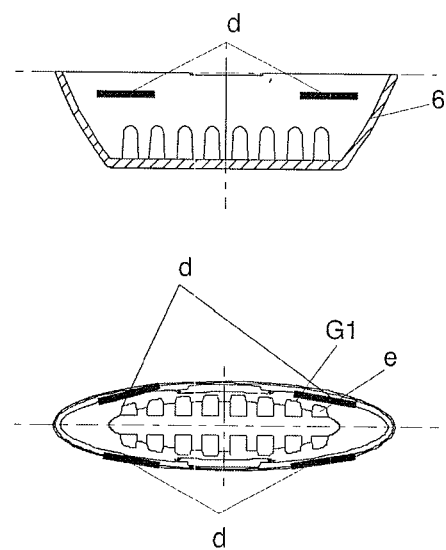
FIG. 8 views of the cartridge C lower cap 6.
Figure 9:
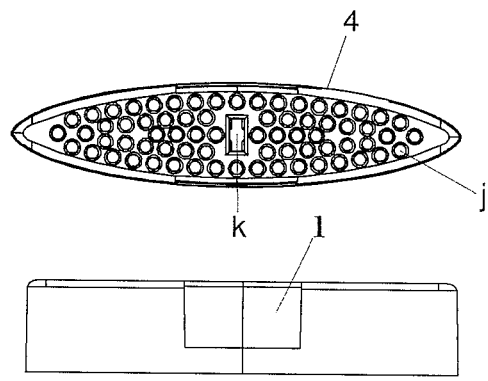
FIG. 9 views of the cartridge C upper cap 4.
Figure 10:
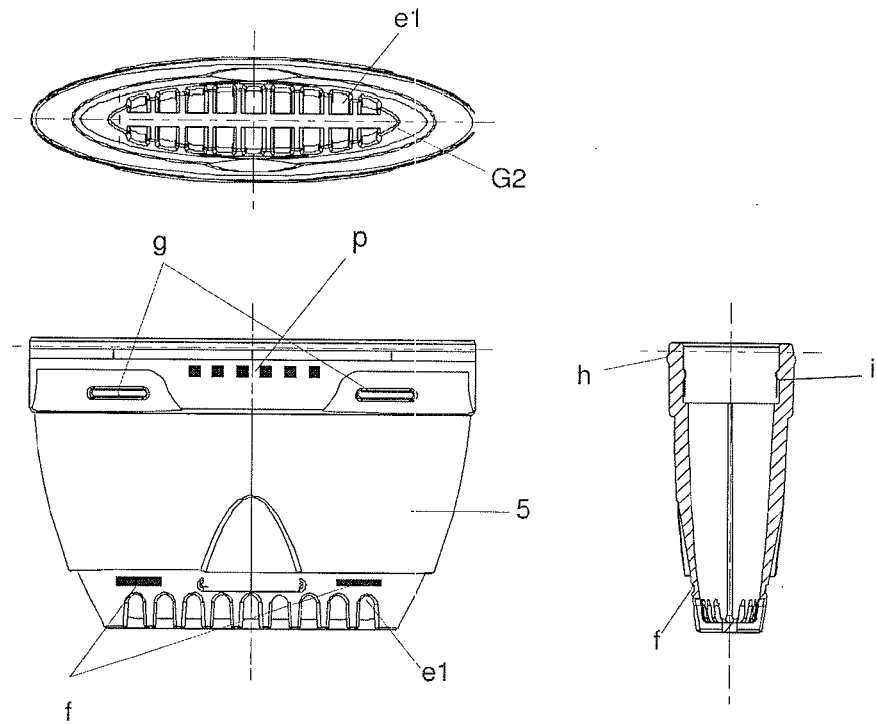
FIG. 10 views of the cartridge C body.
Figure 11:
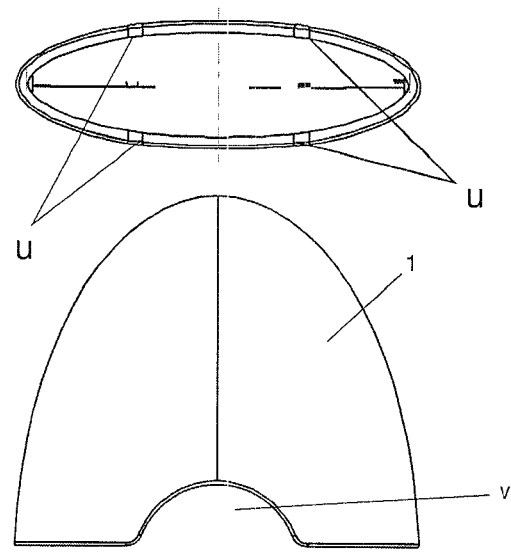
FIG. 11 views of the device upper cap 1.

Considering D the flow direction of the inhaled agent, as it can be noticed in FIGS. 1 and 2, it can be considered that said device presents a lower part A and an upper part B.

In order to fulfill the requirements for function and use, the device is elliptical in shape in the frontal, lateral and transversal plane.

The lower cap 7 is found at the lower part A of the device. Progressing further towards the upper limit of the device the cartridge C is found inside said cap 7 of the device. Said cartridge C is made up of the lower cap 6, the body 5 and the upper cap 4. Inside said cartridge C, salt crystals are introduced.

Between the lower cap 6 and the body 5 of cartridge C, an absorbent material strip 6a is mounted, soaked with essential oil (menthol, eucalypt, fir tree etc.) and used only for aromatherapy, depending upon the intended use of the device.

Progressing further towards the upper part B, the adapter 2A for nasal inhaling or the adapter 2 for oral inhaling is optionally mounted, over the upper cap 4 of cartridge C. In case the adapter 2 for oral inhaling is used, a membrane 3 is mounted inside the upper cap 4, as one-way valve.

The two adapters (oral 2 and nasal 2A) are provided with an area P for advertising.

At the upper part B, the device is closed by means of a protection cap 1 which protects the oral adapter 2 or, as case may be, the nasal adapter 2A.

In order to fulfill the requirements for function and use, the lower cap 7 of the device is semi-elliptical in shape. According to the direction of the airflow that passes through the strip 6a, made of an absorbent material and intended for aromatherapy and further on through the mass of salt crystals placed inside the cartridge C, to get into said adapter 2 or 2A, the lower cap 7 presents at its lower part a grid G0 made up of apertures a to allow access of the air inhaled by the user. At the lower part of cap 7, precisely at said apertures a, said cap 7 is provided with blades b for directing the admitted air. Said blades b also disperse the admitted air.

Four horizontal lugs c are provided inside said lower cap 7 to allow said cartridge C to be fastened and secured against accidental disassembling inside said lower cap.

The lower cap 6 of cartridge C has a processed grid G1 for the passage of the inhaled airflow towards the inhaling adapters. Said grid G1 comprises two rows, each containing 8 apertures e, processed on both sides of said cap. Antipodal horizontal lugs d are provided inside the lower cap 6, to allow the lower cap 6 to be fastened and secured from being accidentally disassembled from the cartridge body 5.

Between the lower cap 6 and the body 5 a strip of an absorbent material 6a can be mounted, whereon the user may place, or not, essential oils for aromatherapy. This procedure will considerably improve the efficacy of the salt therapy, because together with saline aerosols it maximizes the therapeutic efficacy for superior respiratory airways.

At the lower part of said body 5 of cartridge C, there is the grid G2, similar to G1 and made up of an assembly of apertures e1, processed on both sides thereof.

Said apertures e1 have the same purpose, namely that of allowing the access of the inhaled air passing through the mass of salt crystals situated inside the body 5 of the cartridge C, towards the adapters 2, 2A in the upper part of the device.

On the external surface of said body 5 and over the grid G2, two antipodal horizontal cavities f are provided and in the upper part of said body 5, on the external surface thereof, four channels g are processed, the horizontal lugs e of the lower cap 7 protruding inside said channels g.

At the upper edge of said cartridge body 5, on the exterior surface, an annular lug h is provided to hold, as the case may be, the oral adapter 2 or nasal adapter 2A, and, on the interior surface of said body 5 in the upper part, two antipodal spurs i are provided to hold the upper cap 4 of cartridge C.

Figure 13:
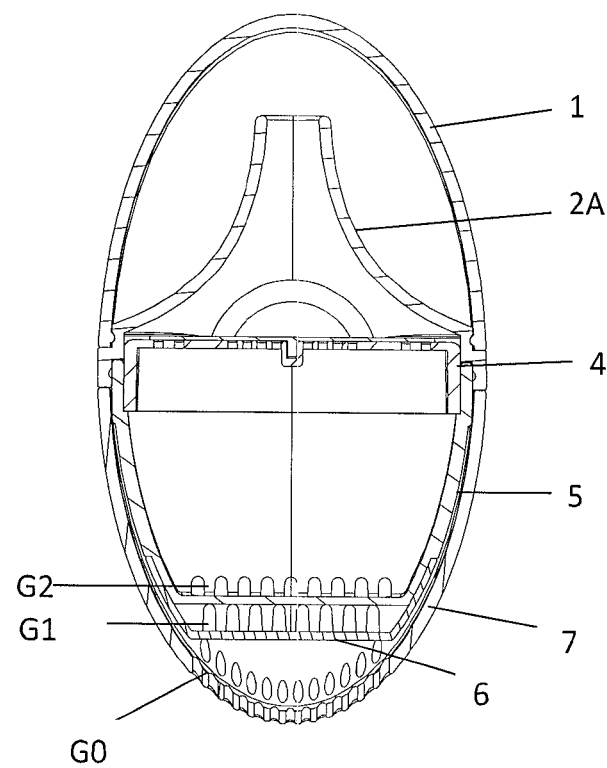
FIG. 13 section through the complete nasal device.
Figure 14:
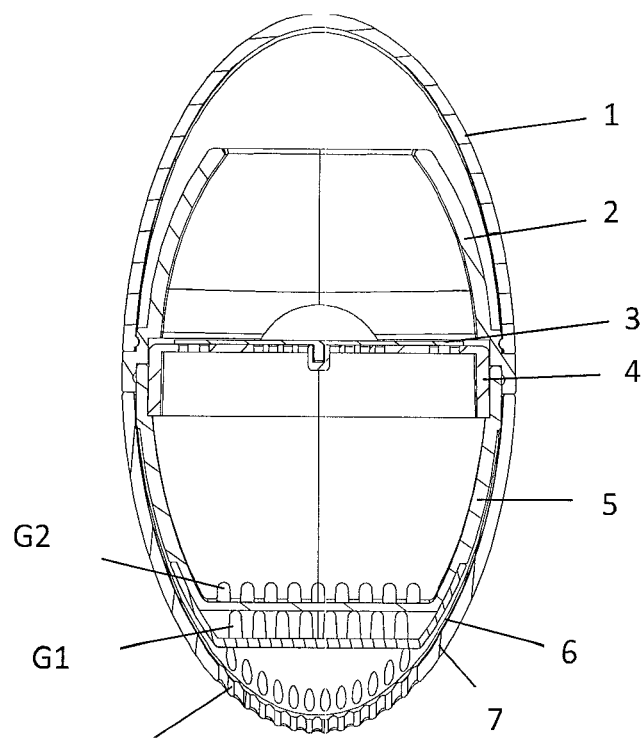
FIG. 14 section through the complete oral device.
Figure 15:
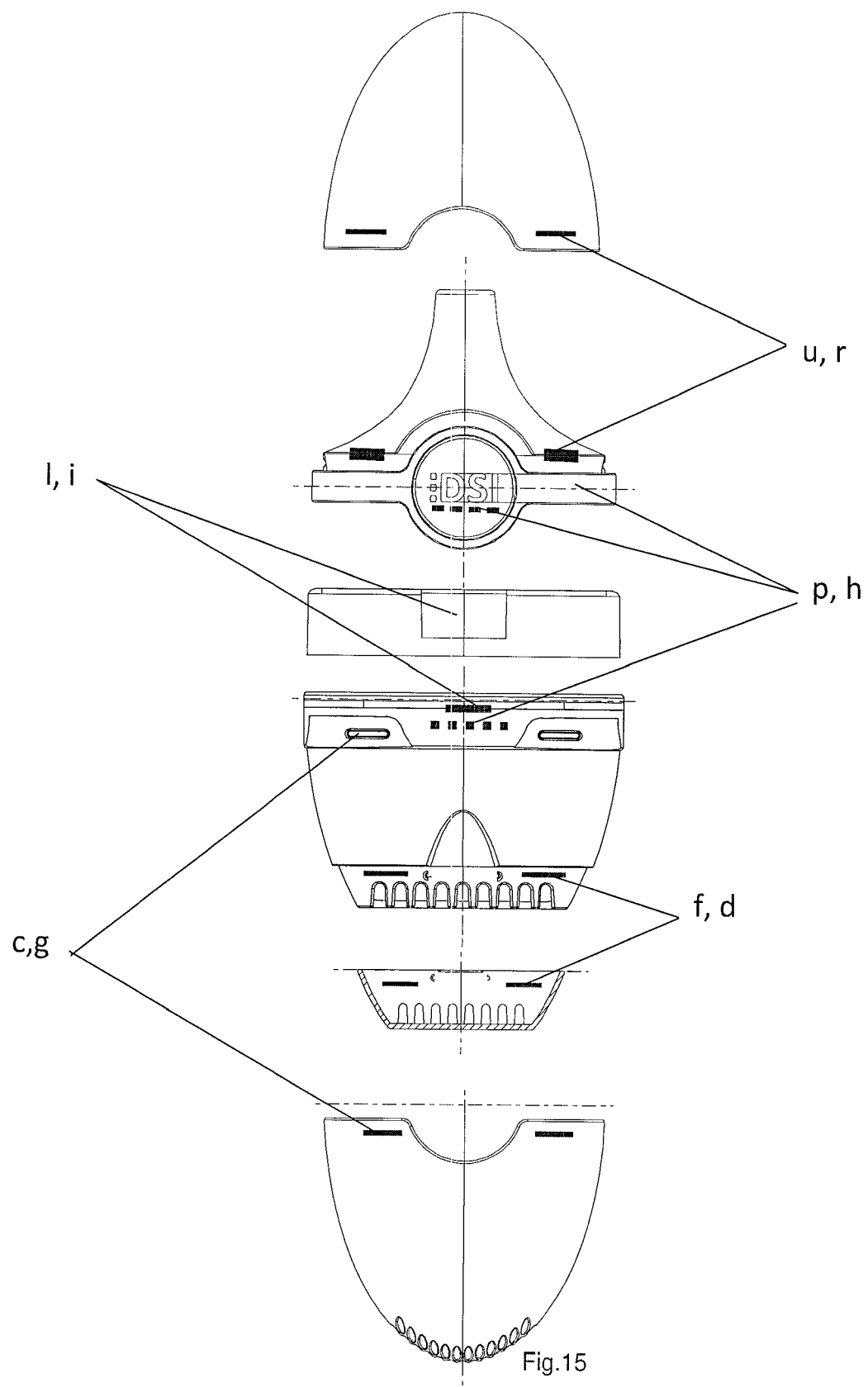
FIG. 15 mechanical means for the securing and fastening of the device components.

When the device is assembled, the grid G2 of the body 5 of said cartridge C is located inside the lower cap 6, as in FIG. 13 or 14.

Inside the body 5 of said cartridge C and at its upper part, the upper cap 4 of cartridge C is mounted. The salt mass traversed by the inhaled airflow is located under said cap 4.

The upper cap 4 is elliptical in shape and has on its base surface a processed grid G3 made of cylindrical apertures j to allow the passage of the inhaled air. At the center of said grid G3 a recess k is provided wherein a membrane 3 is fastened having the role of a one-way valve. On the external surface of the antipodal cap 4, an area 1 corresponding to the spurs i from the interior surface of said cartridge body 5 is disposed, said area allowing said cap 4 to be fastened inside said body 5.

Figure 12:
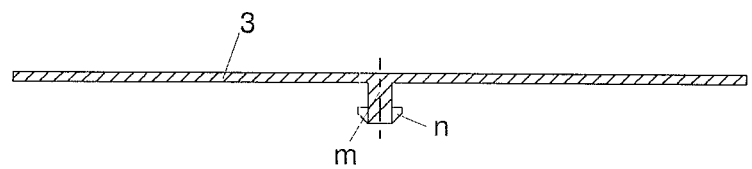

The membrane 3 according to FIG. 12 is made of a flexible material and it is elliptical in shape, similar to the base surface of the upper cap 4. Said membrane 3 has a leg m and ears n for fastening and fixing said membrane 3 inside the recess k on the upper cap 4. In the same time, said membrane 3 allows the device to remain sealed and functioning over a long period of time. Due to the flexible material it is made of, said membrane 3 easily closes down upon exhalation and rises up upon inhalation, functioning as a one-way valve.

Further on, an adapter 2 for oral inhaling is mounted over the sub-assembly of components that form the cartridge C and over said membrane 3. According to the need, the nasal adapter 2A is mounted on said cartridge C, this adapter having a specific shape and size appropriate to nasal inhaling.

When the oral inhalation is contemplated, the oral adapter 2 has an approximately semi-elliptical shape with an oval aperture o processed in its center. At its lower part, said adapter 2 has a second aperture s of a larger size, corresponding in shape and size to the upper cap 4 and the cartridge body 5.

When the nasal inhalation is contemplated, the nasal adapter 2A has in its center a processed circular aperture t at the upper part and an aperture s1 at the lower part, said aperture s1 being of a larger size and corresponding in shape and size to the upper cap 4 and the cartridge body 5.

Both adapters 2 and 2A have on their internal surface a channel p which corresponds to the annular lug h of said cartridge body 5 and on their external surface two antipodal spurs r to hold said upper cap 1 of the device.

The mounting of the adapters 2 or 2A on the assembly of the cartridge C is performed by means of the channel p and the annular lug i, specific processings present both inside said adapters and on the external surface of said body 5 of cartridge C, as it may be seen from FIGS. 1, 2, 4, 6 and 10. The overall size of the parts are so calculated as both fastening and sealing therebetween due to the material contraction is obtained when they are assembled one inside the other.

Adapters 2 and 2A for oral and nasal inhaling respectively, are each provided with an area P for advertising.

At the upper part B of the bi-functional device, adapters 2, 2A are covered with a protection cap 1. Said cap 1 is semi-elliptical in shape and covers the inhaling adapter mounted on the cartridge. Its shape and size are selected in such a manner as to obtain an almost perfect sealed closure of the device, closure provided by means of two fastening elements u antipodally disposed on the internal surface of the upper cap 1. The protection cap 1 is also provided with opposing cutouts v corresponding to areas P intended for advertising.

By providing an elliptical shape to the device and implicitly to its components, the inventors intended to achieve an easy handling, ergonomics, a secure assembling and, disassembling for long periods of time, whenever necessary. At the same time, the adapters 2 and 2A have a shape that when in use, it perfectly suits the mouth or the nose, respectively.

Having taken into account the circulation of the airflow from its entry point at the inlet part of the device to the inhaling adapter of the device, the inventors positioned the apertures a, e, e1 of parts 7, 6 and 5 in such a manner as to obtain the desired circulation of the air.

The salt therapy of the upper respiratory airways is maximized by combining said therapy with aromatherapy, i.e. the air inhaled by the user first passes through the apertures a of the lower cap 7 and apertures e of the lower cap 6 of cartridge C, then through the strip made of an absorbent material 6a soaked with therapeutic essential oils for aromatherapy and thereafter, the aromatized air passes through the salt crystals, an aromatized salty air being formed which makes the therapy of the upper respiratory airways more effective.

The invention claimed is:

1. A bi-functional homeopathic salt crystal inhalation device comprising a lower part and an upper inhalation part, wherein the lower part comprises a lower cap and a cartridge configured to contain salt crystals, the cartridge comprises a lower cartridge cap, a filter of absorbent strip, a cartridge body containing the salt crystals and an upper cartridge cap, the upper inhalation part comprises an inhalation adapter which is configured to mount over the upper cartridge cap and an inhalation adapter protective cap, wherein the lower cap, the lower cartridge cap, the cartridge body and the upper cartridge cap include grids having apertures for the passage of inhaled air from the lower part of the device to the upper inhalation part.

2. The bi-functional inhaling device according to claim 1, wherein the inhalation adapter is one of an inhalation adapter for nasal inhaling which is configured to be mounted over the upper cartridge cap or an oral inhalation adapter which is configured to be mounted over the upper cartridge cap.

3. The bi-functional inhaling device according to claim 2, wherein the oral adapter has an oval aperture at its center or the nasal adapter has a circular aperture at its upper part.

4. The bi-functional inhaling device according to claim 2, wherein the oral inhalation adapter has a channel processed on an internal surface to secure and hold the oral inhalation adapter in the upper cartridge cap and two antipodal spurs on an external surface to secure and hold said upper cartridge cap.

5. The bi-functional inhaling device according to claim 2, wherein said the oral inhalation adapter is provided with an for advertising.

6. The bi-functional inhaling device according to claim 2, wherein in the upper part of the bi-functional device, the oral inhalation adapter is covered with said inhalation adapter protective cap, wherein said inhalation adapter protective cap is semi-elliptical in shape and embraces the oral inhalation adapter mounted on the cartridge, said closure of the device being performed by fastening elements antipodally disposed on the internal surface of the upper cap of the device, wherein said protection cap is also provided with opposing cutouts which correspond to areas intended for advertising.

7. The bi-functional inhaling device according to claim 2, wherein a membrane is fixed on a base surface of the upper cartridge cap, having the role of a one-way valve.

8. The bi-functional inhaling device according to claim 2, wherein said salt crystals are natural salt crystals that are introduced inside said cartridge, in a space created between the lower cartridge cap, the upper cartridge cap and the cartridge body.

9. The bi-functional inhaling device according to claim 2, wherein the grid of the lower cap is a processed grid that is formed of apertures to allow the access of the inhaled air inside said lower cap, wherein blades for directing admitted air and horizontal lugs for securing the cap to the cartridge are provided at said apertures.

10. The bi-functional inhaling device according to claim 2, wherein the grid of the lower cartridge cap is a processed grid at the lower part of the device, the processed grid being formed of apertures to allow the access of inhaled air inside said lower cartridge cap, wherein blades for directing the admitted air and horizontal lugs for securing the lower cartridge cap to the cartridge are provided at said apertures.

11. The bi-functional inhaling device according to claim 1, wherein a membrane is fixed on a base surface of the upper cartridge cap, having the role of a one-way valve.

12. The bi-functional inhaling device according to claim 11, wherein the grid of the upper cartridge cap is made up of cylindrical apertures for the passage of the inhaled air and the upper cartridge cap has at its center a recess wherein said membrane is secured on an antipodal external surface being provided for partly mounting said upper cartridge cap inside the cartridge body.

13. The bi-functional inhaling device according to claim 12, wherein said membrane is made up of a flexible material and the membrane is elliptical in shape, being provided with a leg and ears to have the membrane secured into the upper cartridge cap.

14. The bi-functional inhaling device according to claim 1, wherein said salt crystals are contained in a space created between the lower cartridge cap, the upper cartridge cap and the cartridge body.

15. The bi-functional inhaling device according to claim 1, wherein said grid of the lower cartridge cap is a processed grid at the lower part of the device, said processed grid being formed of apertures to allow the access of the inhaled air inside said lower cartridge cap, wherein blades for directing admitted air and horizontal lugs for securing said lower cartridge cap to the cartridge body are provided at said apertures.

16. The bi-functional inhaling device according to claim 15, wherein said processed grid has apertures processed on both sides of the grid and disposed on two proximal rows, and said horizontal lugs are antipodal horizontal lugs on the inside of the lower cartridge cap.

17. The bi-functional inhaling device according to claim 1, wherein between said lower cartridge cap and body of said cartridge~a strip of absorbent material soaked with essential oil is mounted for aromatherapy.

18. The bi-functional inhaling device according to the claim 1, wherein the grid of the cartridge body made up of an assembly of apertures and antipodal horizontal cavities on the external surface of said cartridge body and channels at its upper part, said cartridge body having on its upper edge a processed annular lug with spurs being disposed on its internal surface to hold the upper cartridge cap partly inside said cartridge body.

19. The bi-functional inhaling device according to claim 1, wherein essential oil drops for aromatherapy are placed over the salt crystals deposited in the cartridge.

* * * * *